(12) United States Patent
Scotto et al.

(10) Patent No.: US 11,148,110 B2
(45) Date of Patent: Oct. 19, 2021

(54) PRODUCTION OF A SOLID CHEMICAL PRODUCT

(71) Applicant: Casale SA, Lugano (CH)

(72) Inventors: Andrea Scotto, Breganzona (CH); Stefano Reggiori, Brenta (IT); Serena Gabbiadini, Milan (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/611,069

(22) PCT Filed: Apr. 30, 2018

(86) PCT No.: PCT/EP2018/061021
§ 371 (c)(1),
(2) Date: Nov. 5, 2019

(87) PCT Pub. No.: WO2018/202617
PCT Pub. Date: Nov. 8, 2018

(65) Prior Publication Data
US 2020/0164325 A1    May 28, 2020

(30) Foreign Application Priority Data
May 5, 2017  (EP) .................................... 17169652

(51) Int. Cl.
*B01J 2/04* (2006.01)
*B01J 2/16* (2006.01)
(Continued)

(52) U.S. Cl.
CPC ................. *B01J 2/04* (2013.01); *B01J 2/003* (2013.01); *B01J 2/16* (2013.01); *C07C 273/02* (2013.01)

(58) Field of Classification Search
CPC .................. B01J 2/16; B01J 2/04; B01J 2/003
See application file for complete search history.

(56) References Cited

U.S. PATENT DOCUMENTS

| | | |
|---|---|---|
| 2,979,421 A | 4/1961 | Rissman et al. |
| 4,842,790 A | 6/1989 | Nunnelly |
| (Continued) | | |

FOREIGN PATENT DOCUMENTS

| | | |
|---|---|---|
| EP | 2 305 371 A1 | 4/2001 |
| EP | 2 077 147 A1 | 7/2009 |
| (Continued) | | |

OTHER PUBLICATIONS

International Search Report issued in connection with PCT/EP2018/061021.

(Continued)

*Primary Examiner* — Mary Lynn F Theisen
(74) *Attorney, Agent, or Firm* — Akerman LLP

(57) ABSTRACT

Method for solidifying a chemical product (10) which is in melt form, comprising the following steps: subjecting a first stream (10a) of said chemical product to a prilling stage, with production of prills (12) of varying diameter; feeding said prills (12) to a screening device, which separates them according to their diameter into at least a first fraction (13) and a second fraction (14), the average diameter of the prills of said first fraction (13) being smaller than the average diameter of the prills of said second fraction (14); subjecting a second stream (10b) of said chemical product and the first fraction (13) of prills to a granulation stage, with the production of granules (16).

7 Claims, 1 Drawing Sheet

(51) Int. Cl.
*B01J 2/00* (2006.01)
*C07C 273/02* (2006.01)

(56) References Cited

U.S. PATENT DOCUMENTS

| | | | |
|---|---|---|---|
| 5,569,315 A | | 10/1996 | Konig et al. |
| 2010/0285214 A1* | | 11/2010 | Zardi .......................... B01J 2/16 427/213 |
| 2012/0231277 A1* | | 9/2012 | Roos .......................... B01J 2/16 428/403 |

FOREIGN PATENT DOCUMENTS

| | | |
|---|---|---|
| EP | 2 497 567 A1 | 9/2012 |
| RU | 2170720 C1 | 7/2001 |
| WO | 9501858 | 1/1995 |

OTHER PUBLICATIONS

International Preliminary Report on Patentability issued in connection with PCT/EP2018/061021.

* cited by examiner

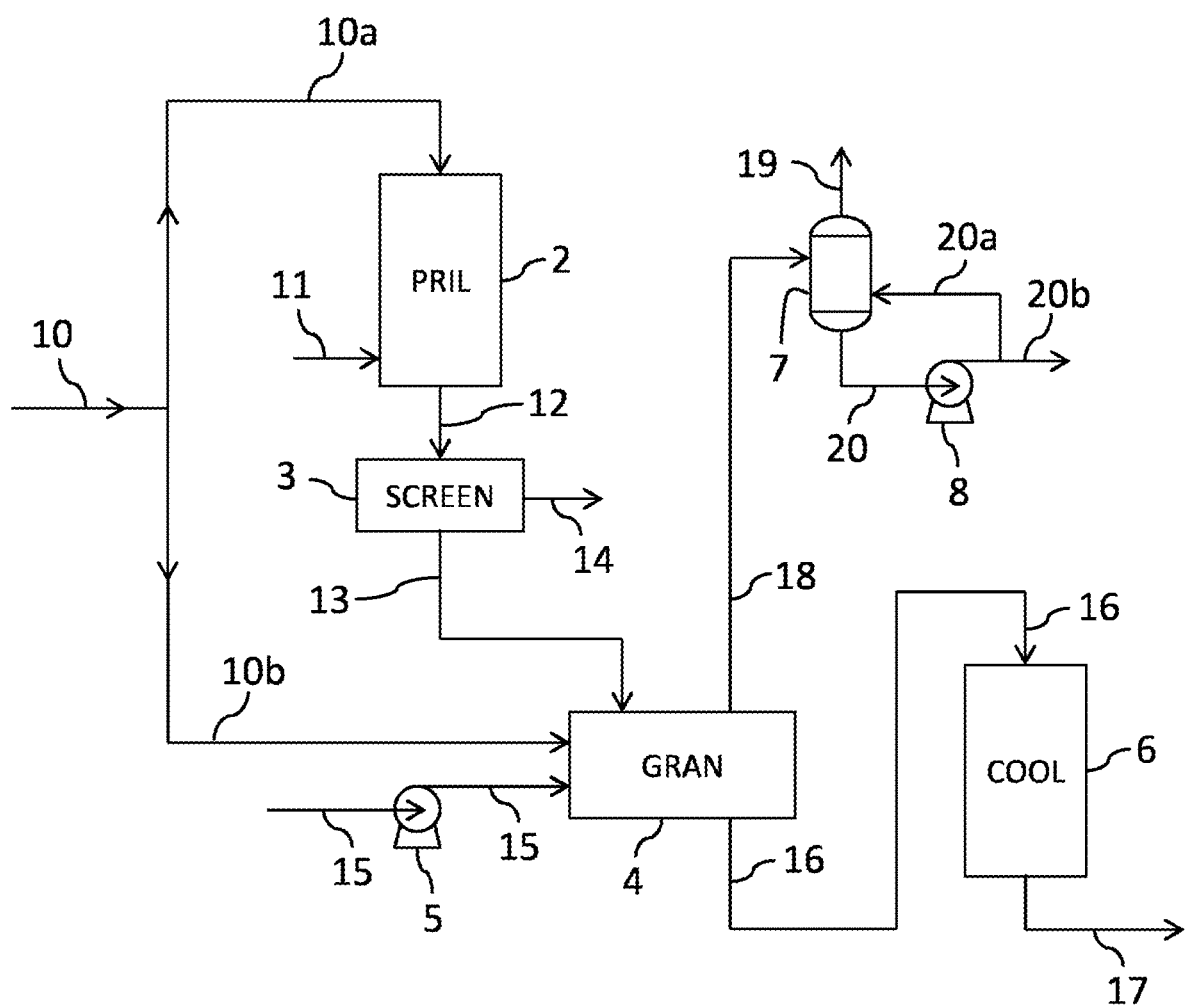

PRODUCTION OF A SOLID CHEMICAL PRODUCT

CROSS-REFERENCE TO RELATED APPLICATIONS

This application is a national phase of PCT/EP2018/061021, filed Apr. 30, 2018, and claims priority to EP 17169652.9, filed May 5, 2017, the entire contents of both of which are hereby incorporated by reference.

FIELD OF APPLICATION

The invention relates to a process for the solidification of a chemical product in melt form to provide a solid in the form of prills or granules. In particular, the invention relates to the field of the production of solid urea.

PRIOR ART

The methods for obtaining a solid chemical product typically include prilling and granulation. The following description will refer, by way of example, to the production of solid urea.

Prilling is performed in a tower where droplets of a urea melt are produced by shower sprinklers or by a rotating drum, and are cooled by air in counterflow until complete solidification. Granulation is a different process wherein the urea melt gradually solidifies inside a granulator. The apparatuses for prilling and granulation form part of the urea finishing (shaping) section.

Prills have small size, generally not exceeding 2 mm, and have low compression and impact resistance, thus being less suitable for storage in bulk form. Granules have, instead, larger average diameter and better mechanical properties, and are therefore regarded as a higher quality product.

Based on the final product so obtained, granulation is therefore considered to be superior to prilling. However, the currently available granulation technologies have high investment costs due to, for example, the need of a certain quantity of solid particles (seeds) for starting the granulation process, and therefore of special equipment, e.g. tablet-making machines, which is generally very bulky and costly. For this reason, the prilling technology is still widely used despite the inferior quality of prills compared to granules.

Prilling towers are typically made of reinforced concrete, with heights from 40 to 100 metres and diameters of up to 25 metres or even greater. These installations are very costly, they are not very flexible and are suitable only for minor modifications, therefore they are inadequate and need costly interventions for example in projects requiring a significant capacity increase. The high costs of said installations also have hitherto discouraged the urea producers from replacing the existing prilling towers with granulators, which would result in abandonment of the prilling towers, leaving them unused and thus entailing a significant economic loss.

In order to exploit the potential of the existing prilling towers and increase the overall capacity of the urea finishing section, it has been proposed in the prior art to connect, in series or in parallel, the prilling towers to granulation units.

EP 2 077 147, for example, describes a finishing section comprising a prilling tower and a granulator connected in series. The prills obtained from the prilling tower are fed to the granulator, where they act as seeds. The granulator acts as a unit for fattening the prills leaving the prilling tower. The solid products leaving the granulator are characterized by an inner part provided with crystallographic structure typical of prills, and by outer layers with variable thickness provided with crystallographic structure typical of granules. Consequently, the solid product of the granulator has mechanical characteristics superior to prills, but not yet equivalent to granules.

SUMMARY OF THE INVENTION

The object of the present invention is to overcome the aforementioned drawbacks of the prior art. In particular, the present invention aims to provide a method which is able to provide a solid product with improved characteristics in terms of dimensions and mechanical strength compared to products provided by conventional methods, while using the existing prilling towers.

This object is achieved with a method for solidifying (shaping) a chemical product in melt form, comprising the following steps:

subjecting a first stream of said chemical product to a prilling stage, with consequent production of prills of varying diameter;

feeding said prills to a screening device, which separates them according to their diameter into at least a first fraction and a second fraction, the average diameter of the prills of said first fraction being smaller than the average diameter of the prills of said second fraction;

subjecting a second stream of said chemical product to a granulation stage and feeding to said stage the first fraction of prills, said prills acting as seeds for the granulation, with consequent production of granules.

The step of feeding the prills produced in the prilling stage to a screening device allows to obtain prills of a suitable diameter and in a proper amount to act as seeds for the granulation stage, thus obtaining from said granulation stage granules with a desired size and mechanical strength.

In some embodiments, said first and second streams may be portions of a same stream of said chemical product, and therefore may have the same concentration. Alternatively, said first and second streams may have different concentration; for example, said second stream may have a smaller concentration that said first stream.

Preferably, the prills belonging to the first fraction have an average diameter which is not greater than 1.7 mm, more preferably ranging from 1 mm to 1.7 mm, and even more preferably ranging from 1.5 mm to 1.7 mm.

According to a preferred embodiment, said second fraction of prills is exported and sent to storage.

The granules obtained from said granulation stage are preferably subjected to cooling and then stored. The granules may be cooled inside the granulator itself or in a cooling apparatus external to the granulator.

Preferably, said granulation stage is performed in a fluid bed fed with air.

Preferably, said chemical product is urea. For the sake of simplicity, the advantages of the invention will be elucidated below with reference to urea.

The method according to the present invention allows to obtain two solid products having different characteristics, which may be exported and stored separately or may be mixed together.

The first solid product is formed by the prills belonging to the aforementioned second fraction, which have an average diameter greater than that of the prills obtained with conventional methods, since they are deprived of the finer prills separated by the screening device, and therefore they have a greater mechanical strength and smaller tendency to form powders especially during handling and transportation.

The second solid product is formed by the granules obtained from the aforementioned granulation stage. They have mechanical characteristics superior to those of the granules obtained with the prills fattening methods, thanks to the fact that the granulation seeds have a smaller diameter. The applicant has found that said second solid product has mechanical properties which are substantially equivalent to those of a granulated product.

Owing to their greater mechanical strength, both these products are less prone to caking and crumbling during transportation and are more suitable for storage in bulk form.

Therefore, the present invention allows to obtain an increase in the average diameter of the prills sent to storage and an improvement in their quality, while using at the same time the finer prills—of lower quality—as seeds for producing granules, which represent a product in great demand on the market.

The method of the present invention, therefore, allows to obtain solid urea of high-quality and high-value with low investment costs.

Further aspects of the invention relate to a solidification (shaping) section of a chemical product which is in melt form, and to a revamping method according to the accompanying claims.

The advantages of the invention will emerge even more clearly with reference to FIG. 1, which shows a schematic diagram of the solidification section of a urea plant according to a preferred embodiment of the invention.

DETAILED DESCRIPTION OF A PREFERRED EMBODIMENT

FIG. 1 shows in schematic form a solidification section 1 of a stream 10 of urea melt coming from a synthesis section (not shown) of a urea plant.

Said solidification section 1 essentially comprises a prilling tower 2 which produces prills of varying diameter, a screening device 3 which separates the finer prills, and a granulator 4 wherein the finer prills act as granulation seeds.

Basically, the solidification section 1 operates as follows.

The prilling tower 2 is fed with a first fraction 10a of urea melt and with air 11 in counterflow. Inside said tower 2, proper shower sprinklers (not shown) produce droplets of urea melt which are cooled by the air 11 until complete solidification, producing prills with a non-uniform diameter. An alternative to said shower sprinklers is a rotating drum.

The prilled product 12 leaving the tower 2 is introduced into the screening device 3, which separates the prills into a first fraction 13 and a second fraction 14. The prills of said first fraction 13 have a smaller average diameter than the prills of said second fraction 14.

The prills of the first fraction 13 are conveyed to the granulator 4 where they act as granulation seeds; the prills of the second fraction 14 are instead exported from the solidification section 1 and stored.

The fraction 14 is also referred to as "large" product of the prilling tower 2, while the fraction 13, which is further treated inside the granulator 4, is also referred to as "fine" product of said tower 2.

In some embodiments, the fraction 14 is cooled in a suitable cooler (not shown) prior to storage.

According to the example shown in FIG. 1, the granulator 4 is of the fluid bed type. It is fed with a second fraction 10b of urea melt and with a stream of cooling air 15 which keeps the bed in the fluid state. The urea melt 10b is sprayed onto the prills (seeds) of the first fraction 13, which gradually increase in size, producing the granules 16. The air flow 15 is fed to the granulator 4 via a fan 5.

The granules 16 are sent to a cooling section 6, wherein they solidify to produce the final product 17 ready for storage.

In a variant, the prilling tower 2 and the granulator 4 are fed with streams of urea melt which do not originate from the same stream. Said streams of urea melt may, therefore, have different concentration. For example, the stream feeding the granulator 4 may have a urea concentration smaller than the stream feeding the prilling tower 2.

The contaminated air 18 leaving the granulator 4 contains urea dust and ammonia and is sent to a scrubbing unit 7, where it is generally treated in the presence of water so as to remove the urea dust and the ammonia. In some cases said contaminated air 18 is also treated in the presence of an acid solution, containing for example sulphuric acid, in order to minimize the ammonia losses.

At the output of the scrubbing section 7, a stream 19 of purified air is emitted into the atmosphere and an aqueous solution 20 containing urea is partially recirculated into the scrubbing section 7 as stream 20a via a pump 8. The remaining portion 20b, instead, is exported.

In case the contaminated air 18 is treated in the presence of water and the aforementioned acid solution, the aqueous solution 20 generally also contains salts (for example ammonium sulphate) in addition to urea.

EXAMPLES

Reference is made to a urea plant comprising a prilling tower. Said plant produces 1'000 MTD of urea melt and said urea melt is supplied to the prilling tower, wherein it solidifies into prills. After revamping, a capacity increase of 50% is obtained resulting in a urea production rate of 1'500 MTD. The additional 500 MTD of urea melt obtained in the revamped plant are supplied to a granulator put in series with the prilling tower.

Comparative Example (Prior Art)

Reference is made to the method of EP 2 077 147. The prills obtained in the prilling tower are all fed to the granulator, wherein they act as granulation seeds, producing the final product.

The average diameter of the prills acting as seeds in the granulator is 2 mm. The average diameter of the final product of the granulator is 2.3 mm, according to the following formula:

$$D = d \cdot \left( \sqrt[3]{\frac{F}{F_2}} \right)$$

wherein:
D=average diameter of the final product of the granulator;
d=average diameter of the prills acting as granulation seeds;
F=total urea melt, namely the urea melt fed to the prilling tower and the granulator;
$F_2$=urea melt fed to the prilling tower.

Said diameter of 2.3 mm is intermediate between that of the prills and that of conventional granules. Accordingly, the final product has mechanical characteristics superior to prills but inferior to granules.

Example of the Invention

The screening device is set to a dimension threshold of the prills of 2 mm.

28% of the prills (i.e. 280 MTD of urea) produced in the prilling tower are sent to the granulator wherein they act as feeds, and 72% of the prills (i.e. 720 MTD of urea) are exported and sent to storage. The remaining 780 MTD of the total urea produced in the revamped plant are exported as granules.

The average diameter of the prills acting as seeds in the granulator is 1.7 mm. The average diameter of the final product of the granulator is 3 mm, according to the formula above.

The final product obtained in the granulator with the method of the invention has a higher average diameter than the final product obtained with the method of the prior art. Accordingly, it has mechanical properties which are substantially equivalent to those of a conventional granulated product.

What is claimed is:

1. A method for solidifying a chemical product which is in melt form, comprising the following steps:
   subjecting a first stream of said chemical product to a prilling stage, with production of prills of varying diameter;
   feeding said prills to a screening device, which separates them according to their diameter into at least a first fraction and a second fraction, the average diameter of the prills of said first fraction being smaller than the average diameter of the prills of said second fraction;
   subjecting a second stream of said chemical product to a granulation stage and feeding to said stage the first fraction of prills, said prills acting as seeds for the granulation, producing granules;
   and wherein said second fraction is exported and sent to storage.

2. The method according to claim 1, wherein the prills of said first fraction have an average diameter not greater than 1.7 mm.

3. The method according to claim 1, wherein said granulation stage is performed in a fluid bed fed with air.

4. The method according to claim 1, wherein said chemical product is urea.

5. A solidification section for a chemical product which is in melt form, comprising at least:
   a prilling tower, which receives a first stream of said chemical product, producing prills of varying diameter;
   a screening device, which separates said prills according to their diameter into at least a first fraction and a second fraction, the average diameter of the prills of said first fraction being smaller than the average diameter of the prills of said second fraction;
   a granulator, which receives a second stream of said chemical product, producing granules;
   a feeding line for feeding said first fraction of prills to the granulator, said prills acting as seeds for the granulation;
   a line for exporting and storing said second fraction of prills.

6. A method for revamping a solidification section for a chemical product which is in melt form, comprising at least:
   a prilling tower, which receives a first stream of said chemical product, producing prills of varying diameter;
   a granulator, which receives a second stream of said chemical product, producing granules;
   a feeding line for feeding said prills to the granulator;
   wherein it comprises at least the following operations:
   a screening device is installed downstream of the prilling tower in order to separate the prills according to their diameter into at least a first fraction and a second fraction, the average diameter of the prills of said first fraction being smaller than the average diameter of the prills of said second fraction;
   modifying said feeding line to feed said first fraction of prills to the granulator; and
   installing a line for exporting and storing said second fraction of prills from the solidification section.

7. The method according to claim 2, wherein the prills of said first fraction have an average diameter ranging from 1 mm to 1.7 mm.

* * * * *